(12) United States Patent
Lee

(10) Patent No.: US 10,065,050 B2
(45) Date of Patent: Sep. 4, 2018

(54) SKINCARE APPARATUS

(75) Inventor: Jong-Dae Lee, Seoul (KR)

(73) Assignee: BOMTECH ELECTRONICS CO., LTD., Seoul (KR)

( * ) Notice: Subject to any disclaimer, the term of this patent is extended or adjusted under 35 U.S.C. 154(b) by 945 days.

(21) Appl. No.: 14/241,763

(22) PCT Filed: Sep. 7, 2012

(86) PCT No.: PCT/KR2012/007212
§ 371 (c)(1),
(2), (4) Date: Feb. 27, 2014

(87) PCT Pub. No.: WO2013/133496
PCT Pub. Date: Sep. 12, 2013

(65) Prior Publication Data
US 2014/0371637 A1    Dec. 18, 2014

(30) Foreign Application Priority Data

Mar. 5, 2012  (KR) .................. 10-2012-0022169
May 23, 2012  (KR) .................. 10-2012-0055061

(51) Int. Cl.
*A61H 1/00* (2006.01)
*A61N 7/00* (2006.01)
*A61H 23/02* (2006.01)

(52) U.S. Cl.
CPC ........... *A61N 7/00* (2013.01); *A61H 23/0245* (2013.01); *A61N 2007/0034* (2013.01)

(58) Field of Classification Search
CPC ........ A61H 23/0245; A61N 2007/0034; A61N 7/00
See application file for complete search history.

(56) References Cited

U.S. PATENT DOCUMENTS

| 4,646,754 A | 3/1987 | Seale |
| 6,740,097 B1 | 5/2004 | Sanchez-Martinez |
| 2004/0024334 A1 | 2/2004 | Boncompte |
| 2005/0203399 A1* | 9/2005 | Vaezy ............ A61B 8/08 |
|  |  | 600/439 |
| 2009/0299234 A1 | 12/2009 | Cho |

(Continued)

FOREIGN PATENT DOCUMENTS

| DE | 20313648 U1 | 12/2003 |
| EP | 1386597 A1 | 2/2004 |

(Continued)

OTHER PUBLICATIONS

Translation of JP 2008093345 listed on IDS filed Feb. 27, 2014.*
(Continued)

*Primary Examiner* — Christopher Cook
(74) *Attorney, Agent, or Firm* — Ohlandt, Greeley, Ruggiero & Perle, LLP

(57) ABSTRACT

A skin care apparatus using ultrasonic vibration is disclosed. The skin care apparatus includes a main body, a vibration unit separably installed on the main body, and an ultrasonic generation portion installed inside the vibration unit to generate vibration, wherein the vibration unit includes a skin contact member provided with a projection that is in a tube shape to transfer the ultrasonic vibration generated from the ultrasonic generation portion to a skin.

7 Claims, 11 Drawing Sheets

(56) References Cited

U.S. PATENT DOCUMENTS

| | | | |
|---|---|---|---|
| 2011/0046521 A1* | 2/2011 | Farrelly | A61N 7/00 |
| | | | 601/2 |
| 2012/0209151 A1 | 8/2012 | Zhou et al. | |
| 2012/0271222 A1* | 10/2012 | Reed | A61M 35/003 |
| | | | 604/22 |
| 2013/0231592 A1 | 9/2013 | Lee | |

FOREIGN PATENT DOCUMENTS

| | | |
|---|---|---|
| EP | 1943999 A1 | 7/2008 |
| JP | 5574826 | 6/1980 |
| JP | 598331 U | 1/1984 |
| JP | 2000116794 A | 4/2000 |
| JP | 2000126310 | 5/2000 |
| JP | 2000233008 | 8/2000 |
| JP | 2004195042 A | 7/2004 |
| JP | 2008093345 A | 4/2008 |
| JP | 2009247811 A | 10/2009 |
| KR | 1020010086925 A | 9/2001 |
| KR | 100809633 B1 | 2/2008 |
| KR | 100830530 B1 | 5/2008 |
| KR | 20080067309 A | 7/2008 |
| KR | 2020090007666 | 7/2009 |
| KR | 1020110000108 | 1/2011 |
| KR | 1020110117476 A | 10/2011 |
| KR | 1020110119468 A | 11/2011 |
| WO | 2011105735 A2 | 9/2011 |

OTHER PUBLICATIONS

European Office Action dated Jul. 5, 2013 corresponding to European Patent App. 12186817.8-1651, 5 pp.
U.S. Office Action dated May 21, 2013 corresponding to U.S. Appl. No. 13/646,230, 8 pp.
Korean Office Action dated Jun. 27, 2012 corresponding to Korean Patent App. No. 10-2012-0022169, 10 pp.
English translation of Japanese Office Action dated Nov. 12, 2013 corresponding to Japanese Patent App. No. 2012-223148, 2 pp.
English translation of European Office Action dated Aug. 5, 2013 corresponding to European Patent App. 12186817.8-1651, 5 pp.
English translation of Japanese Office Action dated Jun. 4, 2013 corresponding to Japanese Patent App. No. 2012-223148, 3 pp.
English translation of Korean Office Action dated Jun. 25, 2013 corresponding to Korean Patent App. No. 10-2012-0055061, 7 pp.
English translation of Korean Office Action dated Apr. 10, 2012 corresponding to Korean Patent App. No. 10-2012-0022169, 10 pp.
U.S. Office Action dated Sep. 26, 2013 corresponding to U.S. Appl. No. 13/646,230, 7 pp.
U.S. Office Action dated May 5, 2013 corresponding to U.S. Appl. No. 13/646,230, 8 pp.
English translation of Japanese Office Action dated Nov. 12, 2013 corresponding to Japanese Patent App. No. 2012-223148, 4 pp.
English translation of International Search Report dated Feb. 19, 2013 corresponding to PCT/KR2012/007212, 4 pp.

* cited by examiner

530

535b 535a

SKINCARE APPARATUS

BACKGROUND OF THE INVENTION

1. Field of the Invention

The present invention relates to a skin care apparatus, and more particularly to a skin care apparatus which can discharge body wastes that are included in a skin to outside and improve the blood circulation by stimulating the skin through ultrasonic vibration.

2. Description of the Related Art

Recently, a skin massage tool which can massage and clean a facial skin using ultrasonic vibration and cure fatness of an abdominal region has been developed and used.

The skin massage tool is helpful to discharge the body wastes included in the skin out of the skin and to perform the smooth circulation of the blood by stimulating the skin through transfer of the ultrasonic vibration to the skin. The skin massage tool is typically provided with an ultrasonic generation member that can generate the ultrasonic vibration, and a vibration transfer member transferring the ultrasonic vibration from the ultrasonic generation member to the skin. For example, skin massage tools using ultrasonic vibration in the related art are disclosed in Korean Registered Patent No. 830530 (hereinafter referred to as "related art 1") and Korean Registered Patent No. 1129308 (hereinafter referred to as "related art 2"). In the related art 1, a vibration transfer member that is in contact with the skin is in the form of a plate with a predetermined thickness. Accordingly, in the case of using the skin massage tool, one side of the vibration transfer member should be kept in contact with the skin. Due to such a utilization method, the massage tool has the problem that it is required to frequently change the skin contact angle at which the vibration transfer member makes contact with the skin portion being massaged depending on various bends of the skin portion being massaged to cause inconvenience in use. Further, since the vibration transfer member is in the form of a plate, a low resonance output may appear in the case where a single ultrasonic oscillator is used.

Accordingly, in order to obtain the resonance output to the extent that body wastes included in the skin can be discharged out of the skin through the plate-shaped vibration transfer member, several ultrasonic vibrators are required to be attached to the vibration transfer member. However, providing of several ultrasonic vibrators as described above causes the manufacturing cost of the product to increase.

In the related art 2, a hot massage device having an ultrasonic vibration element is provided to perform skin massage through the following operation. That is, if an end surface of a main body of the massage device becomes in contact with the skin in a state where the main body is heated by a heating element and the ultrasonic vibration element is operated, the subcutaneous tissue is heated and vibrated. Accordingly, since the subcutaneous fat and body wastes are shifted from a hardened state to a pulpy state that has low viscosity, a seal of blood is expanded and thus a body portion being cured is also expanded. Accordingly, a suction effect that a groove region, which is formed on the end surface of the main body with shallow depth, is filled with the skin occurs to expedite the discharge of the body wastes from the skin pores. According to the related art 2, the end surface of the main body is in direct contact with the skin to achieve an effective heat transfer, and secures a wide contact area with the skin. As described above, the heating element and the ultrasonic vibration element are provided to simultaneously apply heat and vibration to the skin, and the skin that is expanded by such operation (particularly, heating operation) is sucked into the groove formed on the end portion of the main body to fill in the groove. That is, the skin, which is in close contact with the end portion of the main body, is sucked into the groove, and a part of the sucked skin strongly becomes in close contact with the inner periphery of the groove. Due to this, the body wastes discharged from the body portion being massaged are blocked by the end portion of the main body and the inner periphery of the groove, and thus are unable to be smoothly discharged to the outside of the skin.

Further, since the resonance output of the main body that is vibrated by the ultrasonic vibration element is lower than that according to the related art 1 (see FIG. 6), it becomes difficult to expect the skin massage effect through the ultrasonic vibration.

SUMMARY OF THE INVENTION

The present invention has been made to address at least the above problems and/or disadvantages and to provide at least the advantages described below. Accordingly, an aspect of the present invention provides a skin care apparatus which can maximize a resonance output by ultrasonic vibration and smoothly discharge body wastes that are included in a skin out of the skin.

Another aspect of the present invention provides a skin care apparatus which can easily perform message without the trouble of frequently changing the angle of the skin care apparatus with respect to various bends of a skin portion which differ depending on the skin portion being massaged.

According to one aspect of the present invention, a skin care apparatus includes a main body; a vibration unit separably installed on the main body; and an ultrasonic generation portion installed inside the vibration unit to generate vibration, wherein the vibration unit includes a skin contact member provided with a projection that is in a tube shape to transfer the ultrasonic vibration generated from the ultrasonic generation portion to a skin.

A plurality of projections may be repeatedly formed in the tube shape. In this case, the plurality of tube-shaped projections may be radially arranged at predetermined intervals from a center of the vibration unit, or may be dispersedly arranged at predetermined intervals.

The tube-shaped projection may be in the form of any one of a cylinder, an ellipse, and a polygon.

The tube-shaped projection may have a curved portion which is formed in curve on one end portion that is in contact with the skin.

The tube-shaped projection may be made of a metal material.

It is preferable that the vibration unit includes a housing into which the ultrasonic generation portion and the skin contact member are inserted; and a front cover separably coupled to an opening of the housing to prevent the ultrasonic generation portion and the skin contact member from seceding from the housing, wherein the housing is separably coupled to a coupling groove formed on one side of the main body, and the front cover has a through-hole formed thereon to be penetrated by the tube-shaped projection.

It is preferable that the housing is made of an elastic material to minimize the transfer of the ultrasonic vibration generated by the ultrasonic generation portion to the main body.

As described above, according to the present invention, since the projections that are in contact with the skin are formed in the tube shape, the resonance output by the ultrasonic vibration can be maximized and the body wastes that are included in the skin can be smoothly discharged out of the skin through securing the escape space for the body wastes discharged from the skin.

Further, since the plurality of tube-shaped projections are radially and repeatedly arranged or dispersedly arranged, or the end portions of the projections are formed in curve with a predetermined curvature, the skin massage and cleansing can be smoothly performed without the trouble of frequently changing the angle of the skin care apparatus with respect to various bends of the skin portion which differ depending on the skin portion being massaged.

BRIEF DESCRIPTION OF THE DRAWINGS

The above and other aspects, features and advantages of the present invention will be more apparent from the following detailed description when taken in conjunction with the accompanying drawings, in which.

DETAILED DESCRIPTION OF EMBODIMENTS OF THE PRESENT INVENTION

Figure 1:
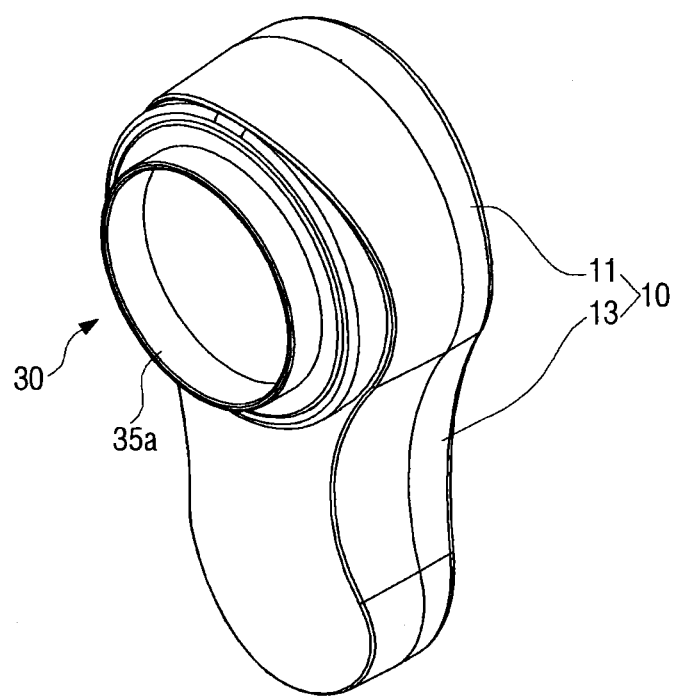
FIG. 1 is a perspective view of a skin care apparatus according to an embodiment of the present invention.
Figure 2:
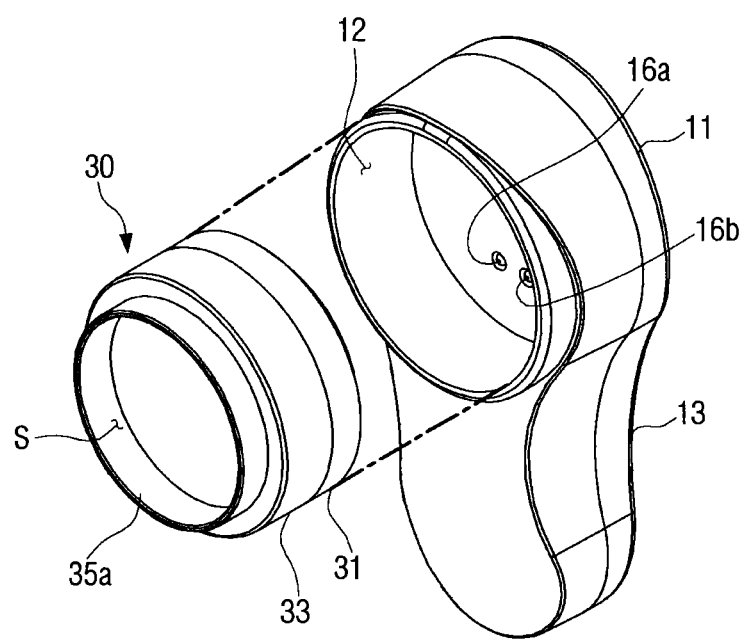
FIG. 2 is an exploded perspective view of a main body and a vibration unit of the skin care apparatus according to an embodiment of the present invention.
Figure 3:
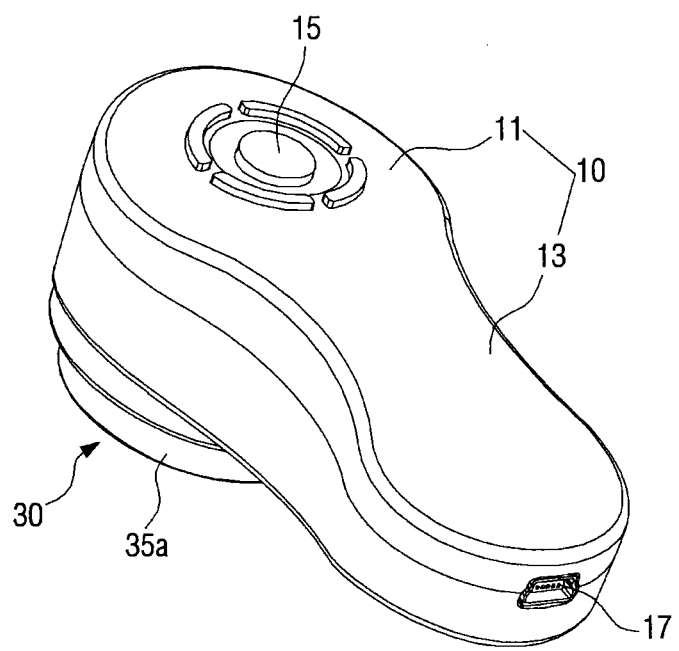
FIG. 3 is a perspective view illustrating the rear surface of the skin care apparatus according to an embodiment of the present invention.
Figure 4:
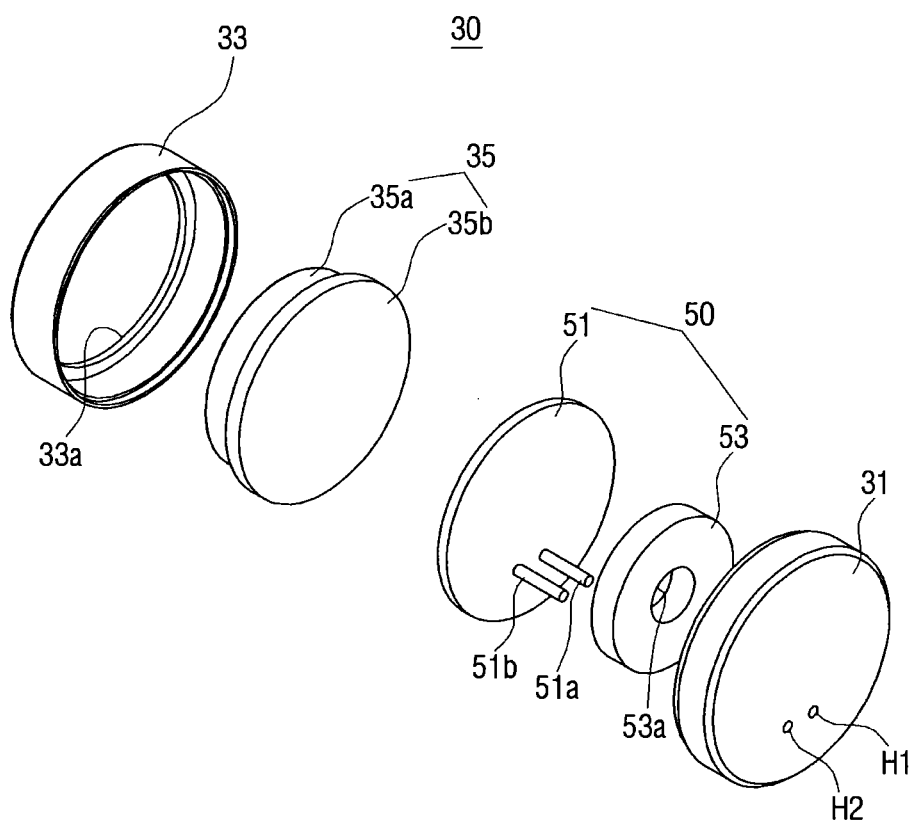
FIG. 4 is an exploded perspective view illustrating the vibration unit illustrated in FIG. 2.

Hereinafter, a skin care apparatus according to an embodiment of the present invention will be described in detail with reference to the accompanying drawings. For reference, in explaining the present invention, detailed descriptions of constructions or processes known in the art may be omitted to avoid obscuring the subject matter of the present invention.

Referring to FIGS. 1 to 4, a skin care apparatus according to an embodiment of the present invention includes a main body 10, a vibration unit 30, and an ultrasonic generation portion 50.

On the inside of the main body 10, a circuit portion (not illustrated) is installed to receive and convert an external power and to control the ultrasonic generation portion 50. On one side of the main body 10, a power supply terminal 17 for supplying the external power to the inside of a PCB is installed. In this case, the terminal may be a USB terminal, and the power can be easily supplied from a computer through the USB terminal.

The main body 10 includes a head portion 11 and a gripping portion 13.

On one side of the head portion 11, a coupling groove 12, to which the vibration unit 30 is separably coupled, is formed. On a bottom surface of the coupling groove 12, a pair of through-holes, from which connection terminals 16a and 16b that are drawn from the circuit portion are exposed, are formed. Further, an operation button 15 is installed on an opposite side of the head portion 11 to the side where the vibration unit 30 is installed. The operation button 15 corresponds to a power button for turning on/off the ultrasonic generation portion 50.

The gripping portion 13 is formed to extend from one side of the head portion 11 with a predetermined length so that a user can grip with his/her hand.

The vibration unit 30 includes a housing 31, a front cover 33, a skin contact member 35, and an ultrasonic generation portion 50.

A housing 31 has an outer diameter that can be pressingly coupled into the coupling groove 12 of the head portion 11, and a space is formed on the inside of the housing 31 to accommodate a skin contact member 35 and the ultrasonic generation portion 50. It is preferable that the housing 31 is made of a synthetic resin or an elastic material having a predetermined elasticity in order to maximally suppress a transfer of ultrasonic vibration that is generated by the ultrasonic generation portion 50 to the head portion 11.

A pair of through-holes H1 and H2 are formed on the rear surface of the housing 31, into which a pair of connection terminals 51a and 51b of an oscillator 51 are inserted. Accordingly, if the vibration unit 30 is inserted into the coupling groove 12 until the rear surface of the housing 31 becomes in close contact with the bottom surface of the coupling groove 12, the pair of connection terminals 51a and 51b of the oscillator 51 are electrically connected to connection terminals 16a and 16b of the circuit portion.

The front cover 33 is separably coupled to an opening on one side of the housing 31 to prevent the skin contact member 35 and the ultrasonic generation portion 50, which are inserted into the inside of the housing 31, from seceding from the housing 31. The front cover 33 has a through-hole 33a formed thereon to be penetrated by a projection 35a of the skin contact member 35.

The skin contact member 35 is made of a metallic material, and is provided with a close-contact portion 35b that is in close contact with the projection 35a and the oscillator 51 of the ultrasonic generation unit 50.

The projection 35a is in a tube shape (for example, in a cylinder shape), and is formed to project from the inner surface of the close-contact portion 35b with a predetermined height. One end portion of the projection 35a is in contact with a skin to transfer the ultrasonic vibration to the skin.

As described above, the projection 35a is tube-shaped and projects with the predetermined height. It is sufficient if the projection 35a has a height to the extent that the skin positioned on the inside of the projection 35a does not reach the inner surface of the close-contact portion 35b when the projection 35a presses the skin with predetermined pressure in a state where one end portion of the projection 35a is in contact with the skin. For this, a predetermined space portion S is formed so that the pores are not clogged by the inner surface of the close-contact portion 35b when the body wastes included in the skin are discharged to the outside of the skin through the pores. Accordingly, the body wastes included in the skin can be naturally discharged through the pores of the skin by the ultrasonic vibration. As described above, by forming the projection 35a in the tube shape, a contact portion thereof with the skin is minimized and a non-contact portion thereof is maximized to minimize an area in which the pores are clogged by the lower end of the projection 35a that is in contact with the skin and thus the body wastes included in the skin are prevented from being discharged out of the skin.

In addition, since the tube-shaped projection 35a has superior resonance characteristics when the ultrasonic vibration is applied thereto, the skin massage can be effectively performed through the ultrasonic vibration even if a single ultrasonic generation portion 50 is provided. The comparison of resonance outputs between the present invention and the related art 1 or 2 will be described with reference to FIG. 6.

The close-contact portion 35b is integrally formed with the projection 35a, and the other surface thereof is in the form of a plane so as to be in mutually close contact with one surface of the oscillator 51. The close-contact portion transfers the vibration generated by the ultrasonic generation portion 50 to the projection 35a.

The ultrasonic generation portion 50 includes the oscillator 51 and a piezoelectric element 53. The oscillator 51 receives an external power through the connection terminal 51a and 51b to perform oscillations. The piezoelectric element 53 becomes in close contact with the other surface of the oscillator 51.

The piezoelectric element 53 is in the form of a ring which has a hole 53a formed in the center thereof. If a voltage is applied thereto, stretching deformation occurs on the outside of the piezoelectric element 53 and on the inside of the hole 53a, and thus the strength of the ultrasonic vibration can be increased.

As described above, according to the skin care apparatus according to an embodiment of the present invention, since the projection 35a that are in contact with the skin are formed in the tube shape, the resonance output by the ultrasonic vibration can be maximized and the body wastes that are included in the skin can be smoothly discharged out of the skin through securing the escape space portion S for the body wastes discharged from the skin.

Hereinafter, examples of projections having various shapes in addition to a simple cylindrical shape will be described with reference to FIGS. 5 to 11. The vibration units 130 to 630 illustrated in FIGS. 5 to 11 have the same configuration as the above-described vibration unit 30 except for the shape of the projections.

Figure 5:
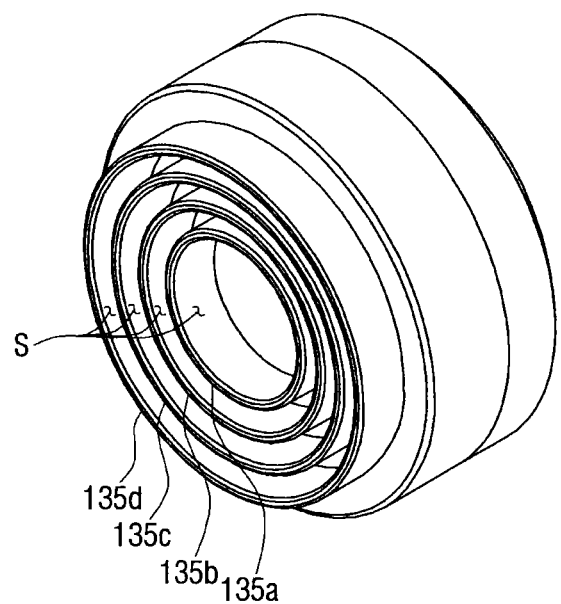
FIG. 5 is a perspective view illustrating a vibration member according to another embodiment.

Referring to FIG. 5, the vibration unit 130 is provided with a plurality of cylinder-shaped projections 135a to 135d repeatedly arranged. The plurality of cylinder-shaped projections 135a to 135d, which have different diameters that become gradually larger toward the outside, are arranged in a manner that the projections 135a to 135d are arranged at predetermined intervals to surround in order the projection 135a that is formed to project from the center of the vibration unit 130.

In this case, the space portions S are formed between the plurality of projections 135a to 135d and on the inside of the projection 135a that is positioned on the innermost side. The space portions S are provided as escape spaces of the body wastes that are discharged out of the skin by the ultrasonic vibration when the skin is massaged.

Further, since the plurality of cylinder-shaped projections 135a to 135d are radially arranged, a user can easily perform the skin massage without the trouble of adjusting the skin care apparatus at specified angles with respect to various bends of the skin portion which differ depending on the skin portion being massaged.

Figure 6:
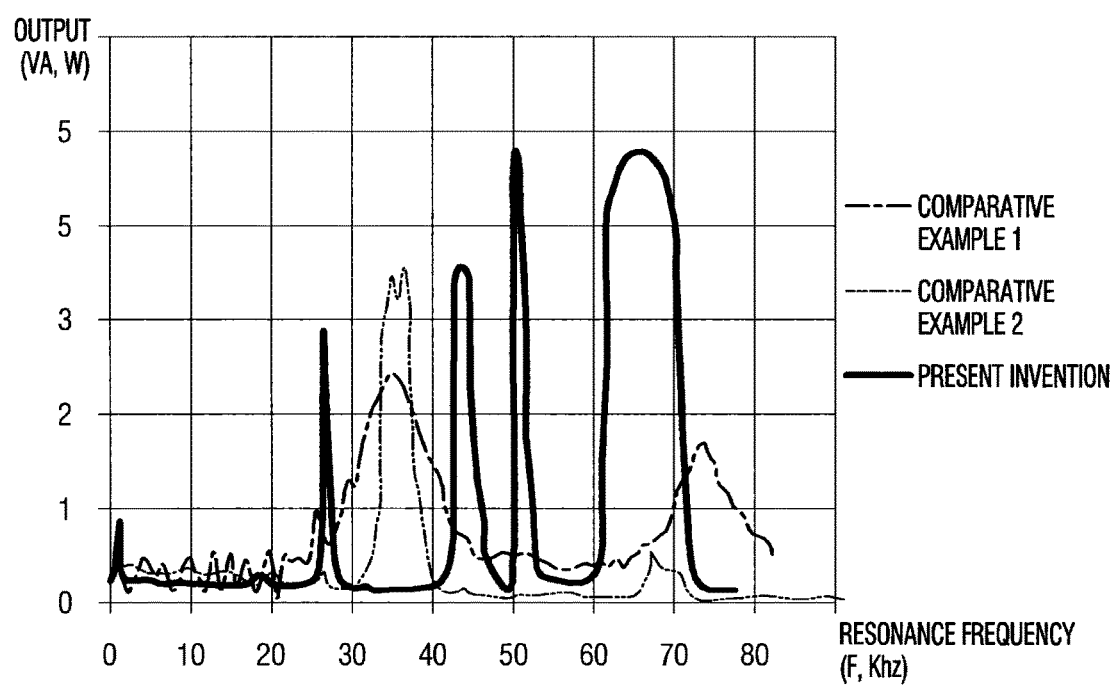
FIG. 6 is a graph comparing outputs of the plurality of tube-shaped projections of the vibration unit illustrated in FIG. 5 with outputs of skin care apparatuses in the related art.

FIG. 6 is a graph comparing outputs of the plurality of tube-shaped projections 135a to 135d repeatedly formed with a thin thickness according to the present invention with outputs of the plate-shaped vibration member (comparative example 1) that corresponds to the related art 1 and outputs of the circular plate-shaped vibration member (comparative example 2) that corresponds to the related art 2. This graph shows the resonance outputs that appear when energy under the same conditions (60V, 300 mA) is applied to the comparative examples 1 and 2 and the plurality of projections 135a to 135d according to the present invention, respectively.

According to the present invention, the graph shows the outputs of a half of the plurality of projections around the center, and the maximum output appears to be near to 5 (VA, W). By contrast, according to the related art 1 and the related art 2, the maximum outputs thereof are 2.5 (VA, W) and 3.5 (VA, W), respectively. In addition, since the plurality of projections 135a to 135d are provided according to the present invention, the output appears over a wide resonance frequency band in comparison to the related art 1 and the related art 2. Accordingly, in the case of inputting the same energy (ultrasonic vibration), a remarkably large resonance output can be obtained through the present invention in comparison to the related art 1 and the related art 2.

Figure 7:
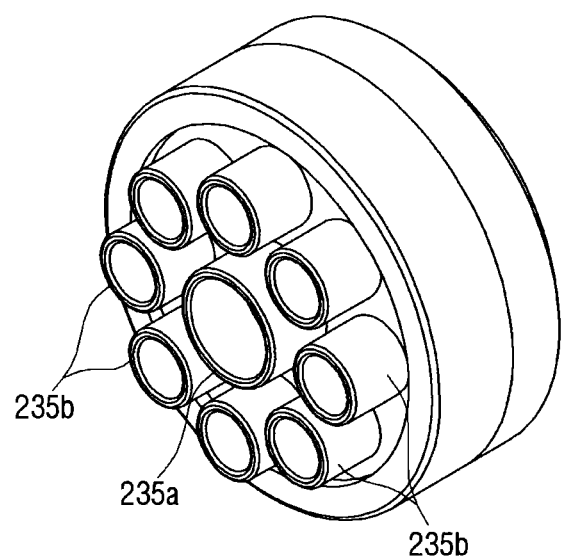
FIGS. 7 to 11 are perspective views illustrating the vibration member according to various embodiments.

Referring to FIG. 7, any one 235a of a plurality of projections 235a and 235b is arranged in the center of a vibration unit 230, and other projections 235b are dispersedly arranged along the circumferential direction around the projection 235a. Even in this case, since the plurality of projections 235a and 235b are arranged to be spaced apart from each other so that predetermined space portions are formed between the projections 235a and 235b, the body wastes included in the skin can be naturally discharged out of the skin in the space portions by the ultrasonic vibration.

Figure 8:
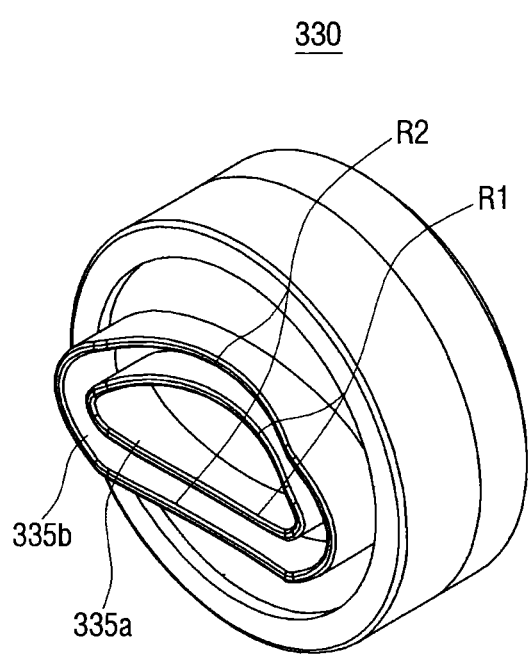

Referring to FIG. 8, a plurality of projections 335a and 335b of a vibration unit 330 are substantially in an elliptical shape, and are repeatedly arranged inside and outside. In this case, the respective projections 335a and 335b are formed to be curved so that end portions R1 and R2 that become in contact with the skin have predetermined curvatures. In this case, the massage can be performed in a state where the plurality of projections 335a and 335b become in close contact with the skin according to the curvatures of the projections.

Figure 9:
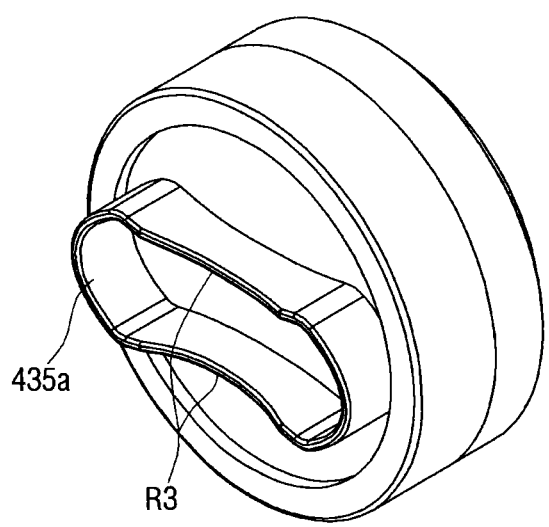

Referring to FIG. 9, a vibration unit 430 has a single projection 435a that is substantially in the form of an elongated hole, and one end portion R3 in the length direction is formed to be curved with a predetermined curvature.

Figure 10:
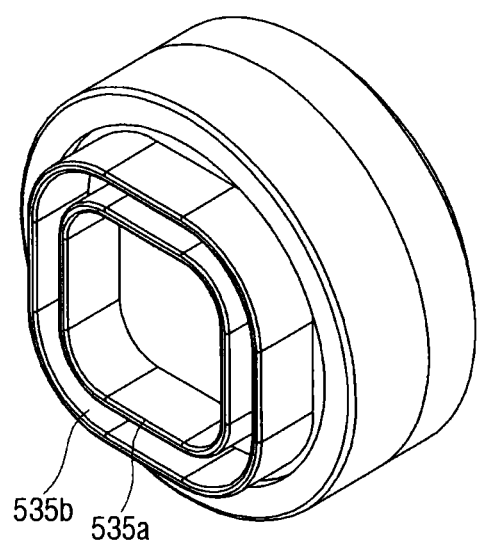

Referring to FIG. 10, a plurality of projections 535a and 535b of a vibration unit 530 are substantially in a rectangular shape, and are repeatedly arranged inside and outside.

Figure 11:
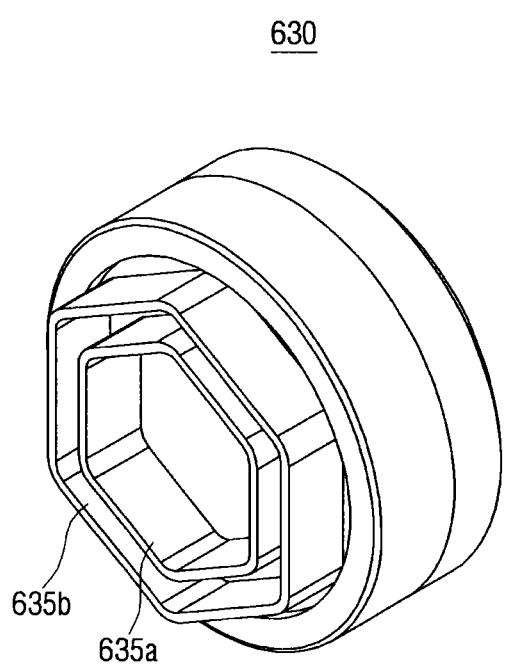

Referring to FIG. 11, a plurality of projections 535a and 535b of a vibration unit 530 are substantially in a hexagonal shape, and are repeatedly arranged inside and outside.

As described above, according to the present invention, since the plurality of projections are arranged in various shapes, the skin massage and cleansing can be smoothly performed without the trouble of frequently changing the angle of the skin care apparatus with respect to various bends of the skin portion which differ depending on the skin portion being massaged. While the invention has been shown and described with reference to certain embodiments thereof, it will be understood by those skilled in the art that various changes in form and detail may be made therein without departing from the spirit and scope of the present invention, as defined by the appended claims.

What is claimed is:

1. A skin care apparatus comprising:
   a main body; and
   a vibration unit separably installed on the main body;
   wherein the vibration unit includes:

an ultrasonic generation portion installed therein to generate vibration;

a skin contact member provided with a projection that is in a tube shape to transfer the ultrasonic vibration generated from the ultrasonic generation portion to a skin;

a housing into which the ultrasonic generation portion and the skin contact member are inserted; and a front cover separably coupled to an opening of the housing to prevent the ultrasonic generation portion and the skin contact member from seceding from the housing, wherein the housing is separably coupled to a coupling groove formed on one side of the main body, and the front cover has a through-hole formed thereon to be penetrated by the tube-shaped projection, wherein the ultrasonic generation portion includes a piezoelectric element provided in a form of a ring which has a hole in a center; and an oscillator in contact with one surface of the piezoelectric element on one side and one surface of the skin contact member on an opposite side, wherein, when a voltage is applied, the piezoelectric element is stretched on an outside of the piezoelectric element and on an inside of the hole to increase a strength of an ultrasonic vibration and wherein the tube-shaped projection has a curved portion which is formed in curve on one end portion that is in contact with the skin.

2. The skin care apparatus as claimed in claim 1, wherein a plurality of projections are repeatedly formed in the tube shape.

3. The skin care apparatus as claimed in claim 2, wherein the plurality of tube-shaped projections are radially arranged at predetermined intervals from a center of the vibration unit.

4. The skin care apparatus as claimed in claim 2, wherein the plurality of tube-shaped projections are dispersedly arranged at predetermined intervals.

5. The skin care apparatus as claimed in claim 2, wherein the tube-shaped projection is in the form of at least one shape selected from the group consisting of: a cylinder, an ellipse, and a polygon.

6. The skin care apparatus as claimed in claim 1, wherein the tube-shaped projection is made of a metal material.

7. The skin care apparatus as claimed in claim 1, wherein the housing is made of an elastic material.

* * * * *